United States Patent [19]

Apostolov

[11] 3,935,066

[45] Jan. 27, 1976

[54] CELL LINES

[75] Inventor: Kostadin Apostolov, London, England

[73] Assignee: Burroughs Wellcome Co., Tuckahoe, N.Y.

[22] Filed: Dec. 13, 1974

[21] Appl. No.: 532,609

Related U.S. Application Data

[63] Continuation of Ser. No. 301,429, Oct. 27, 1972, abandoned, which is a continuation of Ser. No. 108,228, Jan. 20, 1971, abandoned, which is a continuation of Ser. No. 50,289, June 26, 1970, abandoned.

[30] Foreign Application Priority Data

July 3, 1969 United Kingdom............... 33605/69

[52] U.S. Cl. ............................................... 195/1.7
[51] Int. Cl.² ...................... C12B 3/00; C12B 9/00
[58] Field of Search............................. 195/1.7; 1.8

[56] References Cited
UNITED STATES PATENTS
3,871,954  3/1975  Zuckerman........................ 424/89

*Primary Examiner*—Richard L. Huff
*Attorney, Agent, or Firm*—DeLio and Montgomery

[57] ABSTRACT

A human epithelial heterploid liver cell line, such as line WRL 68 which forms individually separated islands or discrete clumps when cultured in a growth medium, has a morphology closely resembling that of hepatocytes of the human liver and a generation time not more than 24 hours, manifests increased production of glycogen in the presence of 1% glucose in the medium, and is capable of supporting viruses.

Such cells may be advantageously used to provide cell cultures for supporting viruses for the preparation of viral vaccines.

4 Claims, 2 Drawing Figures

INVENTOR

Kostadin Apostolov

BY DeLio and Montgomery
ATTORNEYS

CELL LINES

This application is a continuation of application Ser. No. 301,429 filed Oct. 27, 1972. Application Ser. No. 301,429 is a continuation of application Ser. No. 108,228 filed Jan. 20, 1971. Application Ser. No. 108,228 is a continuation of application Ser. No. 50,289 filed June 26, 1970, all now abandoned.

This invention relates to cell lines, in particular to a heteroploid human liver cell line and cultures thereof.

It has been known that certain types of human tissues may be grown in vitro as tissue cultures, and some of these transform into cell lines capable of being propagated and passaged several times on a reasonable scale. Those which had undergone substantial chromosomal changes and became heteroploid in character are particularly useful, since such lines are continuous and can be passaged and multiplied on a very large scale practically any number of times to provide a basis for the industrial production of viruses and corresponding vaccines. Several types of pathogenic viruses infect the liver and multiply therein, and there has been a great demand for a continuous cell line capable of supporting such viruses.

Only fibroblastic diploid cell lines have so far been obtained from liver cells, but these had a limited life span. No continuous heteroploid cell line derived from human liver cells retaining their characteristics has yet been provided to enable researchers to investigate the nature of some pathogens in such cells, to grow them in continuous cultures, and thereby to open the possibility for producing antigenic materials from the propagated and isolated viruses for vaccination and diagnostic purposes. One object of the present invention is to provide such a cell line, in particular a human epithelial liver cell line which contains glycogen and resembles in morphology and in biochemical activity functional liver cells in vivo.

According to the present invention in one aspect therefore there is provided a human epithelial heteroploid liver cell line, such as line WRL 68, which forms individually separated islands or discrete clumps, when cultured in a growth medium, has a morphology closely resembling that of hepatocytes of the human liver and a generation time not more than 24 hours, manifests increased production of glycogen in the presence of 1% glucose in the medium, and is capable of supporting viruses.

Cell line WRL 68 is deposited at the Wellcome Collection of Micro-organisms and Cultures, Beckenham, Kent, England, and also with the American Type Culture Collection at Rockville, Md., United States of America (ATCC accession number CL48).

The type of cell line according to the present invention is heteroploid, i.e. the number of typically human chromosomes is overwhelmingly non-diploid or abnormal, ranging from about 63 to 91, the modal number being about 72. Under the optical microscope the cells are polygonal and epitheloid in appearance and resemble hepatocytes.

So that the invention will be more easily understood and the main features of the cells recognised, features visible under the optical and electronic microscopes of cell line WRL 68 will now, by way of example, be described with reference to the accompanying drawings, in which.

Figure 1:
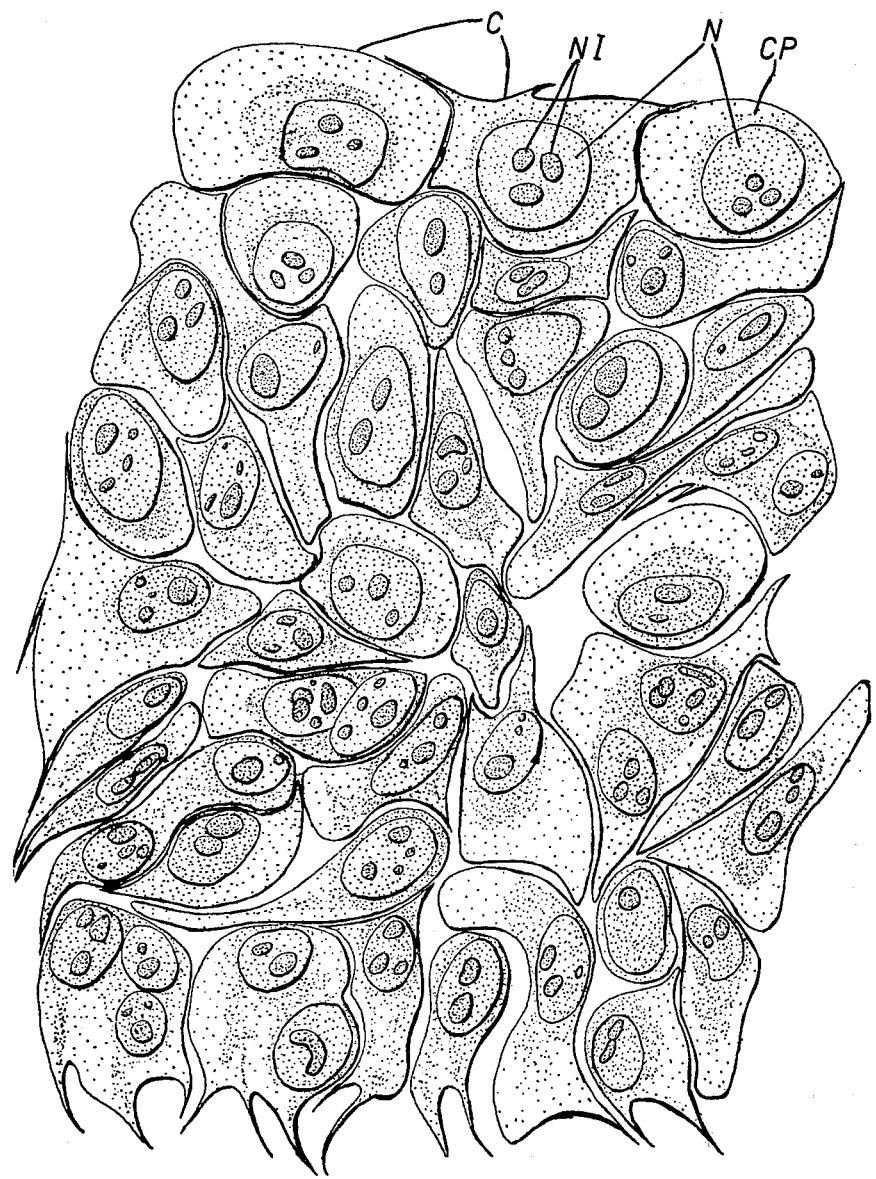
FIG. 1 is a drawing of a discrete clump of cells showing the main features as visible under the optical microscope at a magnification of 2,400 times.
Figure 2:
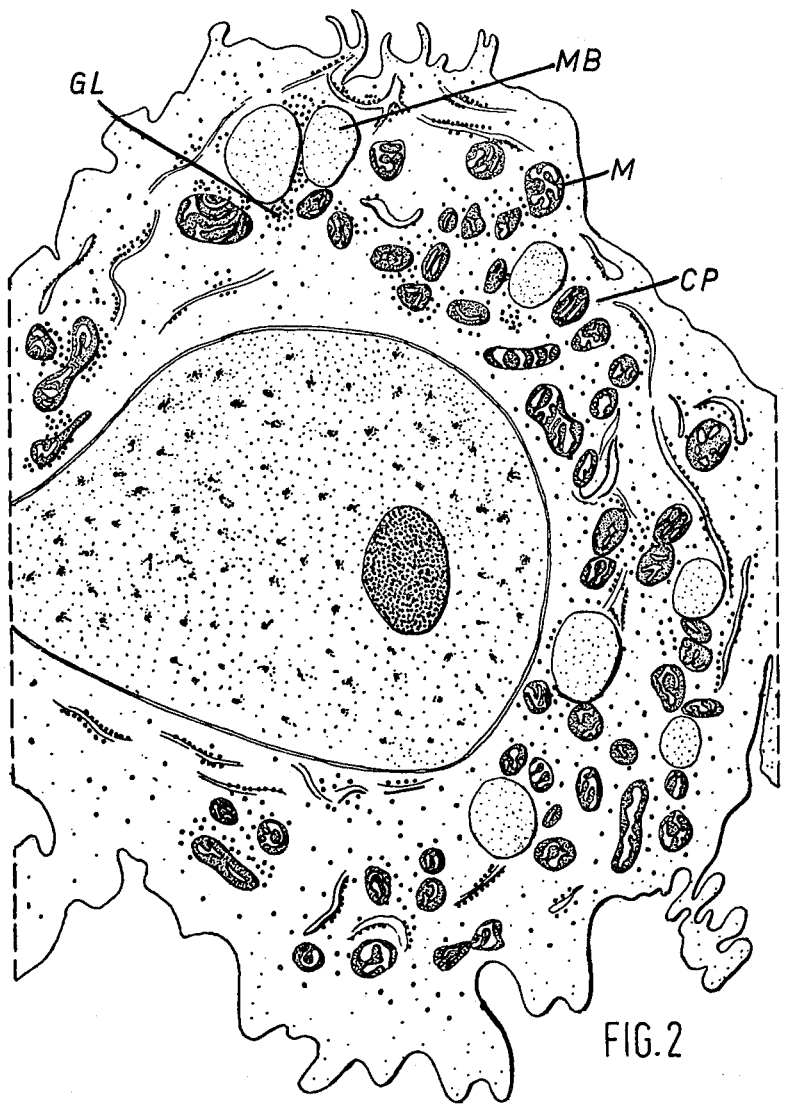
FIG. 2 is a drawing of what is seen under an electron microscope when a section of magnified 19,000 times and examined.

In FIG. 1 individual cells C are shown with rounded nuclei N containing up to five nucleoli NI. Cytoplasm CP surrounds each nucleus N. FIG. 2 shows that under the electron microscope in these sections the cytoplasm CP can be seen to contain many granules MB probably consisting of lipid material. Mitochondria M are very numerous as well as glycogen GL. The appearance in the electron microscope also closely resembles that of typical human hepatocytes, and differs greatly from the usual structure of fibroblastic cells.

Such, and substantially identical cell lines, which can be obtained by those skilled in the art by modifying or cloning the cell lines described and thereby provided by the present invention, without substantially altering the morphological and functional properties of the cell line or those of the culture, are within the scope of the present invention. Although the indicated public availability is the simplest method for obtaining a cell line according to the present invention, it is not altogether impossible or improbable that similar and functionally substantially identical human epithelial heteroploid liver cell lines might be produced by other methods or similar unexpected chance occurrences. Such functionally substantially identical cell lines are biologically equivalent to cell line WRL 68 and are also within the general scope of the present invention.

Cell line WRL 68 has been obtained, as far as we are aware, through a completely unexpected and original spontaneous transformation when human embryo liver tissue was trypsinised and kept in Eagle's Minimum Essential Medium (Eagle H., Science, 1959, 130, 432) mixed with 10% bovine serum at 37°C for a few months.

The cell line readily grows in standard media. Conveniently Eagle's Minimal Essential or Basal (Eagle H., J. Exp. Med., 1955, 102, 595) Media may be used, since these are readily available. As usual, these may be supplemented with bovine serum, especially calf serum. Preferably the usual amount of amino acids and vitamins are increased by a factor of about two. Medium 199 (Morgan J.F., et al., Proc. Soc. Exp. Biol. Med., 1950, 73, 1) may also be used. The generation time is usually around 15 hours under favourable conditions, such as at 37°C. The cell line does not form continuous sheets but grows as islands or discrete clumps which resemble liver lobules. The average dimension of these is between 2 and 3 mm, or about 3 mm.

Biochemically, the cell lines provided by the invention produce glycogen like the functional cells, the hepatocytes of the liver. As all human continuous heteroploid lines, they are oncogenic when tested in hamster cheek pouches.

The cell limes may be used for the cultivation of various human and animal viruses. These include DNA viruses such as vaccinia virus, adenoviruses and the herpes virus, RNA viruses such as poliomyelitis virus, HeLa-cell adapted echoviruses, parainfluenza-1 (Sendai) virus, feline infections enteritis virus, and orboviruses, such as Semliki Forest virus, Sindbis virus.

According to the present invention in another aspect there is provided a method of culturing a heteroploid human epithelial liver cell line, as hereinbefore defined, which comprises maintaining the cells in a nutrient culture medium. In a further aspect the invention provides a method for cultivating viruses, which comprises inoculating the heteroploid human liver cell line or its culture with a virus to which the cells are susceptible, and culturing the cell line, as hereinbefore defined. In a particular aspect there is provided a corresponding cell culture or a virus culture using such cells, which comprises such cell line, or cell line infected with viruses to which the cells are susceptible, in association with a nutrient culture medium.

The viruses obtained in this manner are suitable for further processing in a known manner for instance by passaging in the same or in other cell cultures to provide a purified or attenuated strain and a live vaccine. The antigenic viral material grown according to the invention can also be inactivated by commonly applicable methods to produce an inactivated vaccine. Live or inactivated vaccines are usually presented in association with a pharmaceutically acceptable carrier in a liquid or solid form.

Another possibility is that the cell line according to the present invention can be used in research for instance to investigate the metabolic processes of the liver, or for the production of glycogen or enzymes normally produced by the liver in vivo. Furthermore these cells may act as hosts to human hepatitis viruses which have not yet been successfully grown in any culture in vitro.

The following Examples illustrate the invention:

EXAMPLE 1

A sample of the heteroploid liver cell line WRL 68 representing about $10^5$ to $10^6$ cells was transferred into 1 oz. medicinal flat bottles containing Eagle's Minimal Essential Medium supplemented with 10% v/v calf serum. After 3 days at 37°C maximum development of clumps was observed. 0.5 Milliliter of a suspension of adenovirus 11 in Eagle's Basal Medium, containing about $10^4$ TCID 50 (tissue culture infective doses)ml., was contacted with the cells and the virus was allowed to adsorb for half an hour. The excess of virus was washed off with maintenance medium (without serum), and the culture was incubated at 37°C.

A cytopathic effect typical for adenoviruses was observed after 3 days. The culture was then frozen and thawed to liberate the virus from the cells. The cell debris was filtered off, and the presence of the virus in the medium was demonstrated by haemagglutination with patas monkey red blood cells. The titre was 128, indicating the maximum dilution still showing haemagglutination.

Adenovirus strains 4, 5, 7 and 15 were also grown in the cell line and gave satisfactory titres.

EXAMPLE 2

The Lister strain of vaccinia virus was adsorbed to a culture of the heteroploid liver cell line, as described in Example 1. A typical cytopathic effect was observed after incubation for 24 hours at 37°C. The cell line was also susceptible to the Jenner strain of vaccinia virus and a similar cytopathic effect was observed.

EXAMPLE 3

The following viruses were also successfully grown on the heteroploid liver cell line WRL 68, as described in the previous Examples:

Poliomyelitis virus, echoviruses 2, 7, 9, 11, 15, 17, 20, 23 and 25 previously adapted to HeLa cell cultures, Sendai virus, herpes virus, feline infectious enteritis virus, San Carlos virus, and arboviruses such as the Semliki Forest virus and Sindbis virus.

These viruses show satisfactory antigenicity after adaptation to the human hetroploid liver cell line. Such and other susceptible viruses may therefore be grown on such a cell line and presented as a vaccine in association with a pharmaceutically acceptable carrier, after appropriate inactivation or attenuation according to methods well known in the art.

What we claim is:
1. A cell culture of a human epithelial heteroploid liver cell line, comprising a cell line in association with a nutrient culture medium, said cell line being a human epithelial heteroploid liver cell line, comprising cells characterized as follows:
   a. the cells form individually separated islands or discrete clumps when cultured in a growth medium;
   b. the cells have a morphology closely resembling that of hepatocytes of the human liver;
   c. the cells have a generation time not more than 24 hours;
   d. the cells manifest increased production of glycogen in the presence of 1% glucose in the said growth medium; and
   e. the cells are capable of supporting viruses.

2. A cell culture according to claim 1 wherein the islands or discrete clumps resemble liver lobules.

3. A cell culture according to claim 2, wherein the islands or discrete clumps have an average dimension of between 2 and about 3 mm.

4. A cell culture of a human epithelial heteroploid liver cell line, comprising a cell line in association with a nutrient culture medium, said cell line comprising a human epithelial heteroploid liver cell line, as deposited with the American Type Culture Collection under accession number CL48.

* * * * *

UNITED STATES PATENT AND TRADEMARK OFFICE
CERTIFICATE OF CORRECTION

PATENT NO. : 3,935,066
DATED : January 27, 1976
INVENTOR(S) : Kostadin Apostolov It is certified that error appears in the above-identified patent and that said Letters Patent are hereby corrected as shown below:

On the Title Page, the Assignee should read as follows: --Burroughs Wellcome & Co. (U.S.A.) Inc.--

Column 1, line 65, "microscopes" should read --microscope--.

Signed and Sealed this

Sixth Day of July 1976

[SEAL]

Attest:

RUTH C. MASON
Attesting Officer

C. MARSHALL DANN
Commissioner of Patents and Trademarks